United States Patent [19]
Nickson

[11] Patent Number: 5,961,471
[45] Date of Patent: Oct. 5, 1999

[54] PROBE FOR A BIOPHYSICAL SKIN MEASUREMENT DEVICE

[75] Inventor: Steven W. Nickson, Derry, N.H.

[73] Assignee: Nova Technology Corporation, Portsmouth, N.H.

[21] Appl. No.: 08/858,899

[22] Filed: May 19, 1997

Related U.S. Application Data

[63] Continuation of application No. 08/395,572, Feb. 28, 1995, abandoned.

[51] Int. Cl.[6] ........................................ A61B 5/00
[52] U.S. Cl. ............................. 600/546; 600/547
[58] Field of Search ................... 600/546–548, 600/552–555, 558, 559, 587

[56] References Cited

U.S. PATENT DOCUMENTS

| | | | |
|---|---|---|---|
| 4,155,351 | 5/1979 | Teshima et al. | 128/734 |
| 4,577,640 | 3/1986 | Hofmeister | 128/734 |
| 4,951,683 | 8/1990 | Davis | 128/734 |
| 4,996,993 | 3/1991 | York | 128/734 |
| 5,240,010 | 8/1993 | Weinmann | 128/734 |

*Primary Examiner*—Max Hindenburg
*Attorney, Agent, or Firm*—Pearson & Pearson; George A. Herbster

[57] ABSTRACT

A probe for a biophysical skin measurement device includes: a disposable sensor; a handle for receiving a cable from the measurement device; a socket on the handle electrically interconnected with the cable; and means for removably engaging the disposable sensor device and the socket; when engaged, the sensor device being electrically interconnected with the cable through the socket for providing measurement signals to the biophysical skin measurement device.

22 Claims, 7 Drawing Sheets

PROBE FOR A BIOPHYSICAL SKIN MEASUREMENT DEVICE

This application is a continuation of Ser. No. 08/395,572 filed Feb. 28, 1995 now abandoned.

FIELD OF INVENTION

This invention relates to a probe for a biophysical skin measurement device having a disposable sensor.

BACKGROUND OF INVENTION

Electronic instruments which non-invasively measure biophysical characteristics of the skin, such as moisture level, are used to evaluate cosmetics, personal care products and pharmaceuticals, for example. Additionally, they are used in clinical studies and medical research typically involving a number of subjects.

These electronic instruments use skin testing probes which have permanently attached sensors that are actually physically contacted with each subject's skin. The electronic instruments and skin testing probes are available, for example, from NOVA Technology Corporation, Gloucester, Mass.; I.B.S. Co., Ltd., Japan; and Courage & Khazaka Gmbh, Köln, Germany. The device sold by NOVA allows the probes to be disconnected from the electronic instrument; however, the two foreign manufacturers' probes are hardwired to their electronic instruments.

After each use with a particular subject, especially when used to evaluate wounds or genital areas of the body, a new probe or a sterilized probe must be used to prevent the transmission of contagious diseases from one subject to another. Because the probes are relatively expensive, costing approximately $500 to over $700 a piece, it is generally not economically feasible to keep on hand a large number of probes, thus, a small number of probes must be used which must be sterilized often, especially when there a large number of subjects. This results in a costly and time consuming process both for the users of the probes and their subjects. It is even more difficult when the probes are hardwired to the electronic instruments.

Another problem is that if a different size sensor is desired there must be used either an entirely new probe, in the case of the NOVA device, or an entirely new measurement device, in the case of the German and Japanese devices.

SUMMARY OF INVENTION

It is therefore an object of this invention to provide a probe for a biophysical skin measurement device having a disposable sensor.

It is a further object of this invention to provide such a probe in which the sensor may be disposed of after use with a subject.

It is a further object of this invention to provide such a probe which is inexpensive as compared to probes having permanent sensors now available.

It is a further object of this invention to provide such a probe which reduces the risk of spreading contagious disease among testing subjects and others.

It is a further object of this invention to provide such a probe which reduces testing time and cost.

It is a further object of this invention to provide such a probe in which various disposable sensors may be assigned to particular subjects when the subjects must be tested numerous times.

It is a further object of this invention to provide such a probe which can accommodate a number of interchangeable sensors with various diameters.

This invention results from the realization that a truly efficient and cost effective probe for use with a biophysical skin measurement device can be achieved by providing the probe with a disposable sensor device and means for removably engaging the disposable sensor device with a socket such that when engaged the sensor device is electrically interconnected with a cable through the socket for providing measurement signals to the biophysical skin measurement device.

This invention features a probe for a biophysical skin measurement device. The probe includes a disposable sensor device and a handle for receiving a cable from the measurement device. There is a socket on the handle electrically interconnected with the cable. There are means for removably engaging a disposable sensor device and the socket. When engaged, the sensor device is electrically interconnected with the cable through the socket for providing measurement signals to the biophysical skin measurement device.

In a preferred embodiment the handle may include means for removably interconnecting a cap with the handle for covering the socket and securing the socket to the handle. The means for engaging may include first thread means on the socket and second, complementary thread means on the sensor device for engaging the sensor device and the socket. The sensor device and the socket may be engaged by means of a friction fit. The means for engaging may include two projections on the sensor and two complementary slots in the socket for receiving the projections and securing the projections and sensor to the socket. The sensor device may be at least partially formed of brass. The sensor device may include a first sensor member for interconnecting with one of a first conductor and a second conductor of the cable and a second sensor member for interconnecting with the other of the first conductor and second conductor. The first and second sensor members may be electrical conductors. The second sensor member may be peripherally disposed about the first sensor member and the first and second sensor members may be separated by an insulating member.

This invention further features a probe for a biophysical skin measurement device. The probe includes a disposable sensor device. The probe also includes a handle for receiving a cable from the measurement device. There is a threaded socket on the handle electrically interconnected with the cable. The disposable sensor device has threads complementary to the threads on the socket for removably engaging the threaded socket. When engaged, the sensor device is electrically interconnected with the cable through the socket for providing measurement signals to the biophysical skin measurement device. There is a cap for engaging the handle for covering the socket and securing the socket to the handle.

DISCLOSURE OF PREFERRED EMBODIMENT

Other objects, features and advantages will occur to those skilled in the art from the following description of a preferred embodiment and the accompanying drawings, in which.

Figure 1:
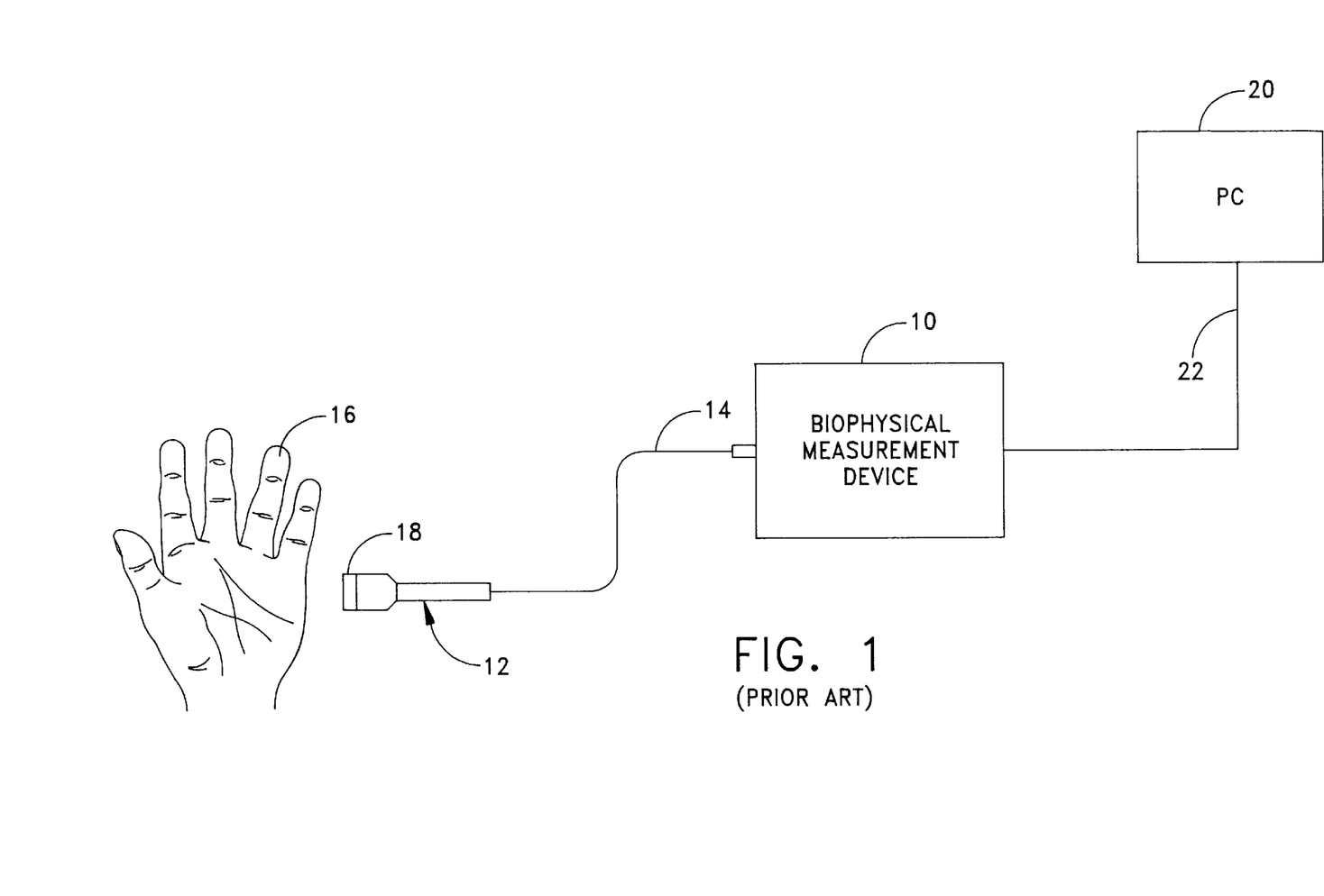
FIG. 1 is a schematic diagram of a biophysical skin measurement system including a prior art probe.

There is shown in FIG. 1 biophysical skin measurement device 10 which may be a dermatological instrument such as a NOVA DPM 9003 sold by NOVA Technology Corporation, Gloucester, Mass. or any similar device. When measurement device 10 is used in conjunction with probe 12 interconnected therewith by means of an elongated cable 14, biophysical properties of the skin on a user's hand 16, such as moisture level, for example, may be made by contacting sensor 18 with the skin on hand 16. Measurement device 10 provides an electrical signal over cable 14 which typically includes a neutral and a "hot" conductor which are interconnected with two separate contact areas on sensor 18. When sensor 18 is energized and is contacted with the skin, measurement device 10 measures the impedance of the skin from which a capacitance value is obtained. The capacitance value is then correlated with a biophysical property of the skin, such as moisture level. This sensor could also be configured with a number of concentric electrodes as described in PCT application, International Publication Number WO 92/06634. Measurement readings can be monitored and stored in personal computer (PC) 20, for example, interconnected with measurement device 10 as shown by means of cable 22. There are other measurement devices supplied by Courage & Khazaka, a German company whose device measures the resistance of the skin and by I.B.S. Co., Ltd., a Japanese company whose device measures the conductance of the skin. However, both use probes similar to probe 12 wherein sensor device 18 is permanently affixed to the probe 12 and measurement device 10. In fact, with these devices the probe is hardwired to measurement device 10 as cable 14 is permanently interconnected with measurement device 10. As discussed above, these probes with their permanently affixed sensors and probes are expensive and if utilized with more than one subject typically must be sterilized to prevent the spread of contagious diseases.

Figure 2:
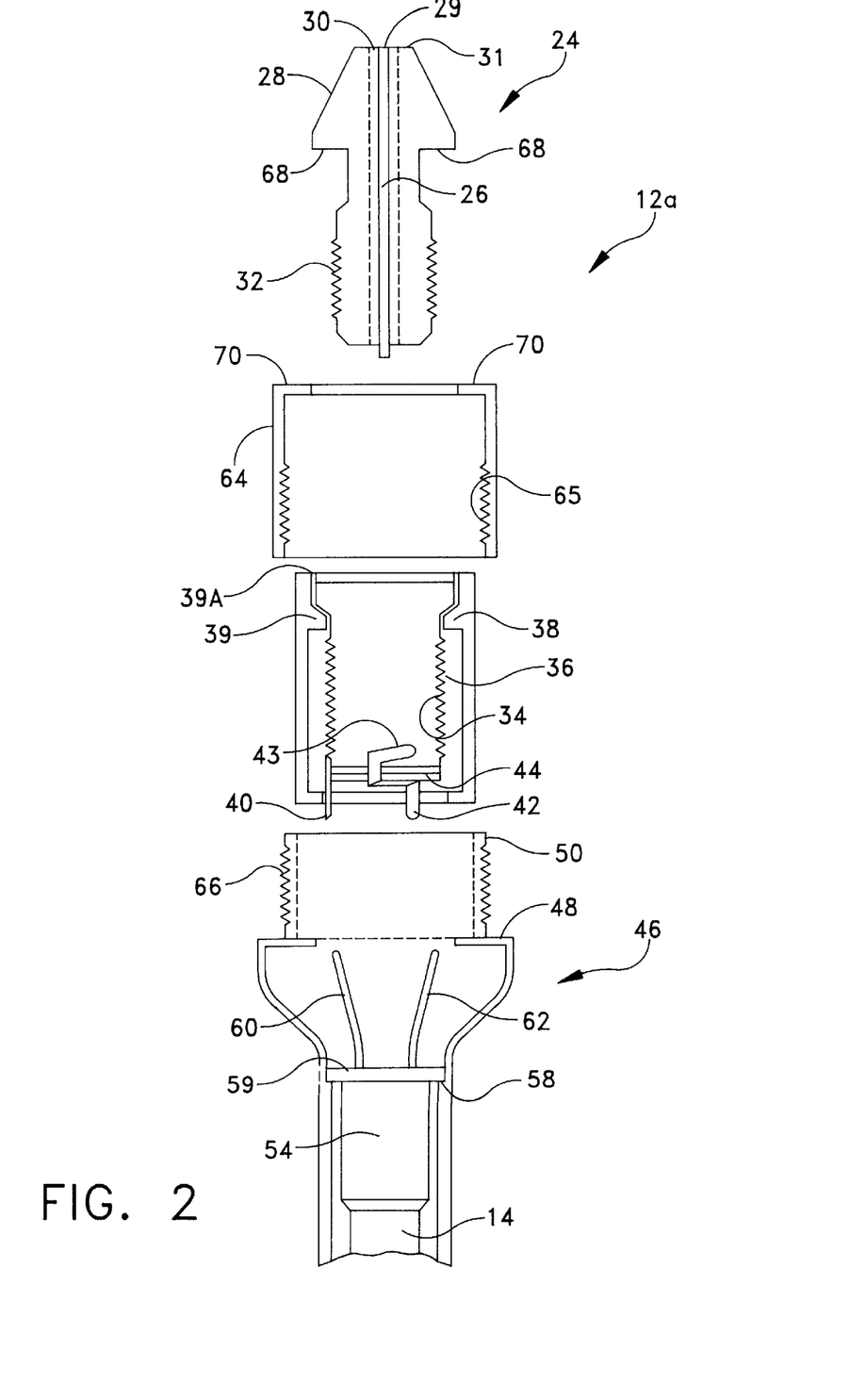
FIG. 2 is an exploded, cross-sectional view of a probe having a disposable sensor according to this invention.

The present invention overcomes these problems by providing a probe 12a, FIG. 2, in which disposable, removable sensor 24 includes central conductor 26 and outer conductor 28 coaxially disposed about central conductor 26 and separated by insulator member 30. Conductors 26 and 28 are typically formed of brass but may be formed of any other suitable conductive material. Central conductor 26 includes a contact surface 29 and outer conductor 28 includes contact surface 31 for contacting a subject's skin. The contact surface of removable sensor 24 may be of varying diameters for different applications. And, since sensor 24 is removable the user may have a number of different size and shape sensors which can be used interchangeably.

Sensor 24 also includes threads 32 which removably engage complementary threads 34 of socket 36 which is contained within socket unit 38 and seated by circumferential ridge 39. Socket 36 typically includes a serrated top edge 39A. Socket 36 also includes outer conductor contact 40 electrically interconnected with threads 36, and central conductor contact 42 having contact member 43 biased to receive central conductor 26 of removable sensor device 24 when engaged. There is an insulating member 44 forming the bottom of socket 36 which electrically isolates contact 42 from threads 34 and contact 40. When removable sensor 24 is engaged with socket 36 threads 32 of sensor 24 engage threads 34 of probe 36 and provide an electrical interconnection between outer conductor 28 and contact 40 and central conductor 26 and contact 42.

Probe 12a also includes a handle 46 which has a handle seat 48 and an extension member 50. Socket unit 38 is disposed within extension member 50 and rests upon seat 48 of handle 46. Within handle 46 is included cable 14 terminating in bushing 54 which is typically shrink wrapped to cable 14. Rim 59 of bushing 54 is seated upon circumferential rim 58 in the interior of handle 46. Within cable 14 are conductor 60 which is the "hot" conductor that is interconnected with contact 40 of socket 36 and the neutral conductor 62 which is interconnected with contact 42 of socket 36. Cable 14 and conductors 60 and 62 are interconnected with the biophysical measurement device 10, FIG. 1, discussed above.

When socket unit 38 is seated within extension 50 of handle 46 cap member 64 is placed over socket unit 38 and its threads 65 are engaged with threads 66 on extension member 50 of handle 46. Cap member 64 covers both socket unit 38 and socket 36 and secures these members in place to handle 46 with rim 70 engaging the top serrated edge 39A. Once cap member 64 is in place removable sensor 24 may be installed or removed from socket 36. When installed, surface 68 of sensor 24 seats flush on rim 70 of cap member 64.

The parts of probe 12a which are not used for electrical conduction, such as handle 46 cap member 64 are typically formed of an electrically insulating material such as plastic.

Figure 3:
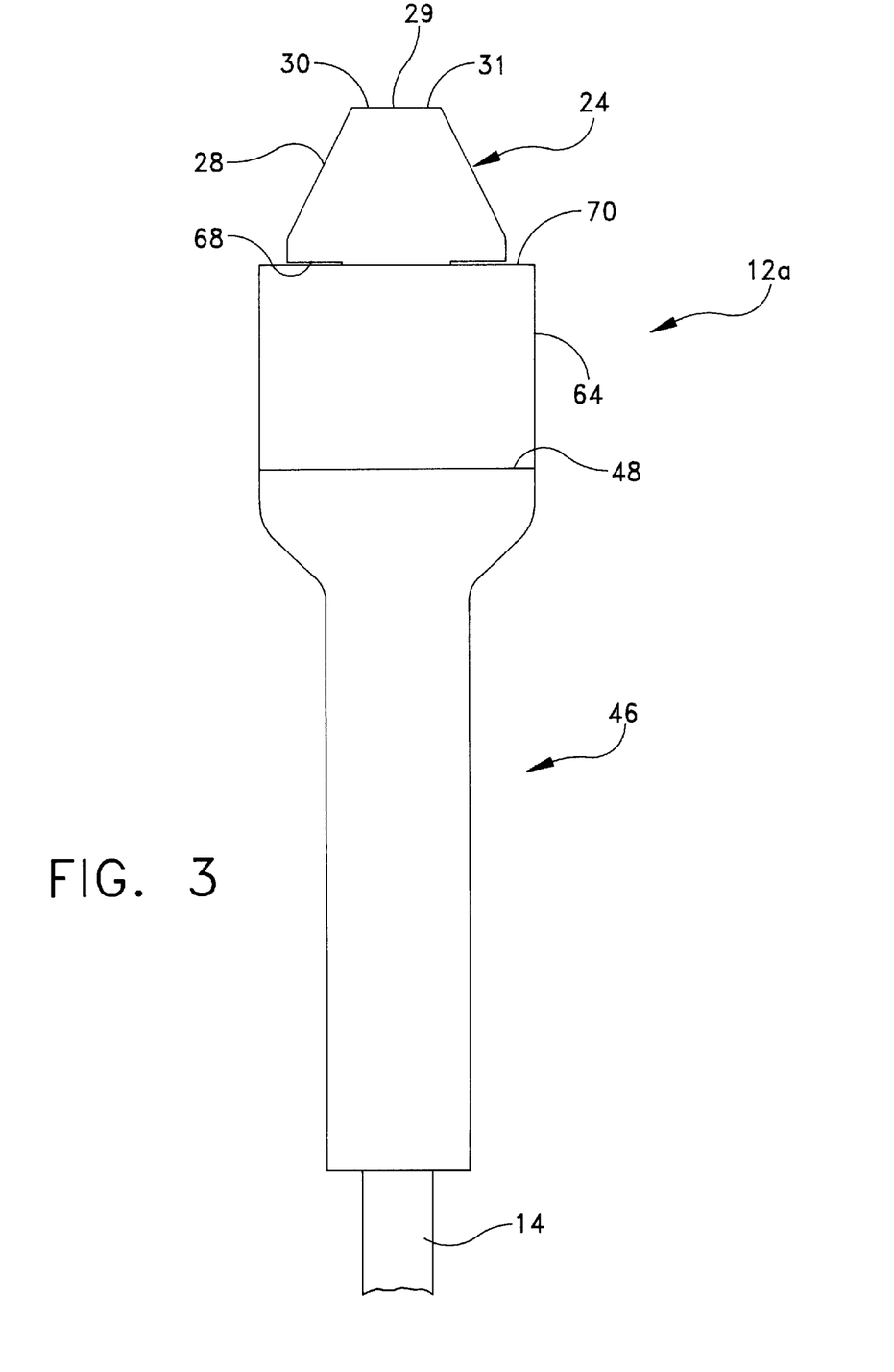
FIG. 3 is a side view of the assembled probe and sensor of FIG. 2.

Probe 12a, FIG. 3, is shown fully assembled with removable sensor 24 installed within socket 36. A slightly different sensor 24a, FIG. 4, includes an outer rim 72 for engaging the underside of rim 70 of cap member 64. The other side of rim 72 engages the top of socket unit 38, not shown in this figure. With this configuration, sensor 24a cannot be removed from socket 36, FIG. 2, until cap member 64 is removed. Sensor 24, FIG. 2, can be installed and removed from socket 36 when member 64 is mounted over socket unit 38.

Figure 4:
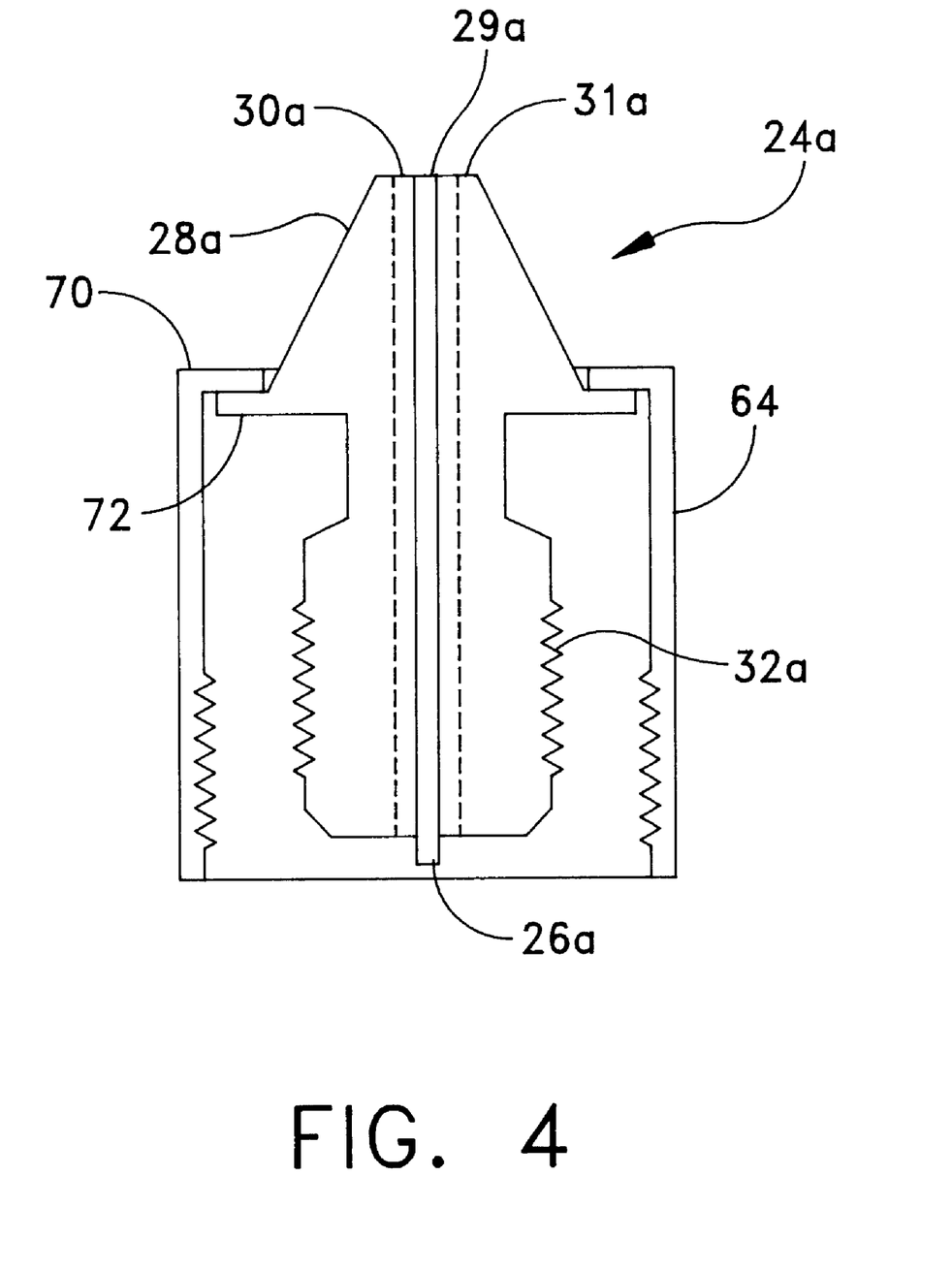
FIG. 4 is a cross-sectional view of an alternative sensor according to this invention.
Figure 5:
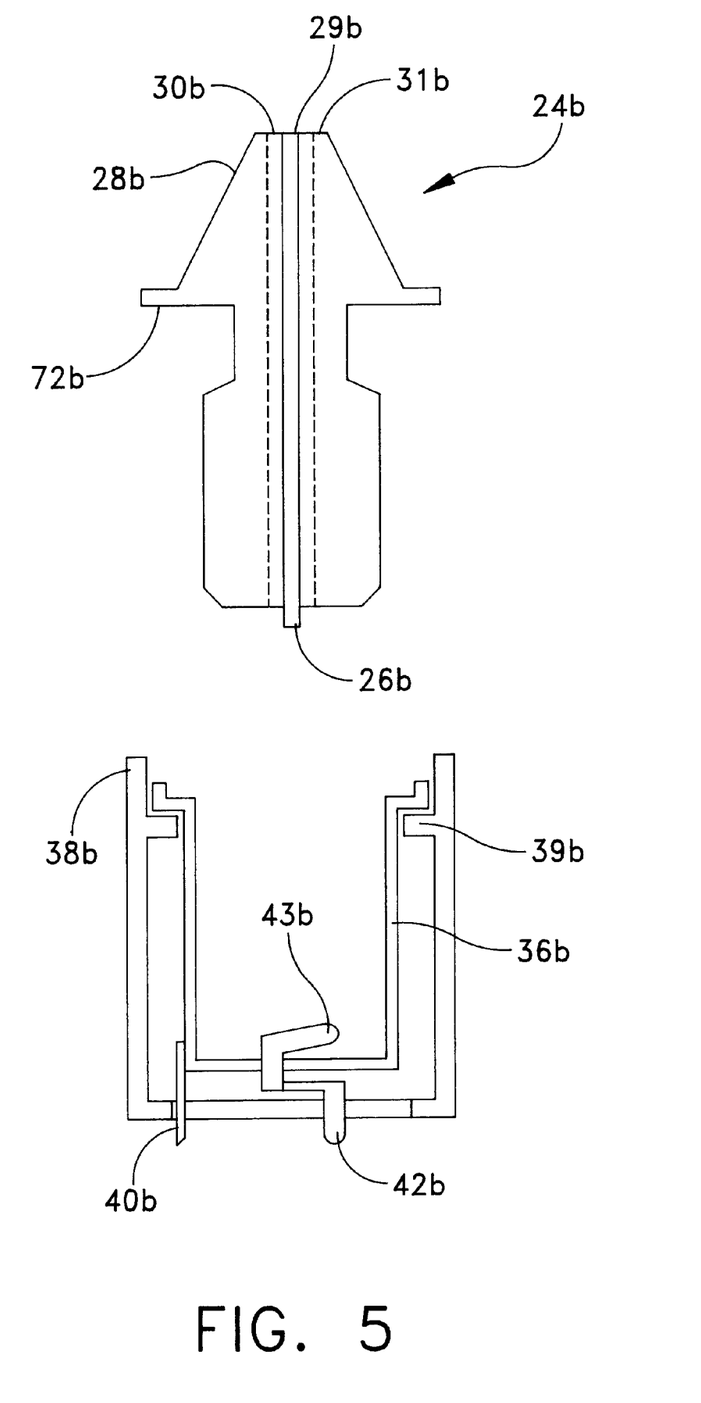
FIG. 5 is a cross-sectional view of another alternative sensor and socket configuration according to this invention.

Sensor 24b, FIG. 5, is configured identically to sensor 24a, FIG. 4, except that sensor 24b includes no threads. Its diameter is slightly larger than the diameter of socket 36b which also does not include threads so that sensor 24b may be removably engaged with socket 36b by means of a friction or interference fit. Sensor 24 and socket 36, FIG. 2, may also be similarly configured.

Figure 6:
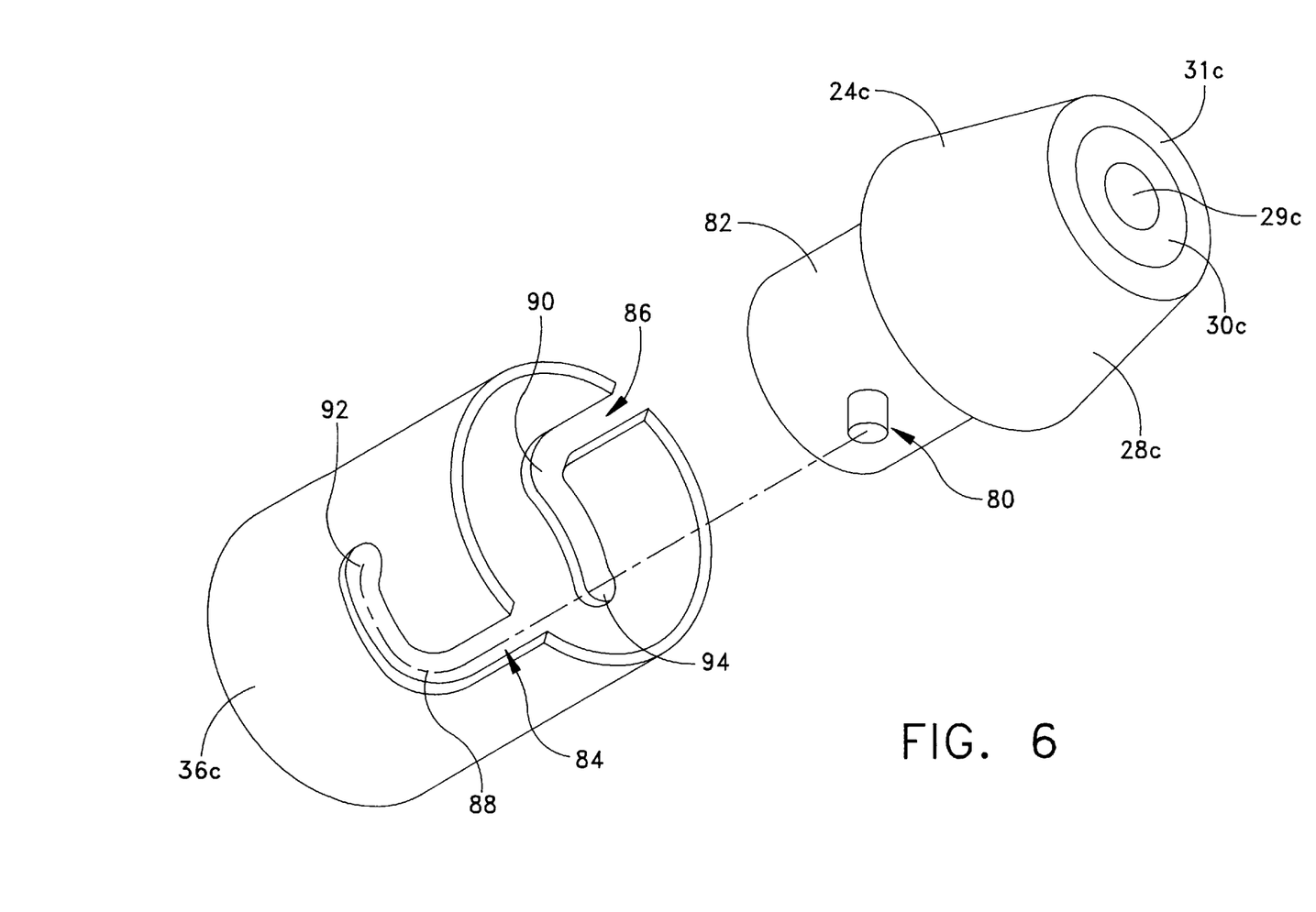
FIG. 6 is a cross-sectional view of yet another alternative sensor and socket configuration according to this invention.

An alternative configuration including sensor 24c and socket 36c is shown in FIG. 6. Sensor 24c includes two bayonet projections 80 spaced 180° apart about surface 82 of sensor 24c. Only one bayonet projection 80 is shown in this figure. Socket 36c includes two curved slots 84 and 86 for receiving bayonet projections 80. When sensor 24c is inserted into socket 36c projections 80 engage the top of slots 84 and 86. As sensor 24c is inserted further into socket 36c, bayonet projections 80 reach points 88, 90 in curved slots 84 and 86, respectively. At this point sensor 24c is rotated in a clockwise direction so that bayonet projections 80 are rotated into a locked position in slot locks 92 and 94 of slots 84 and 84, respectively.

Figure 7:
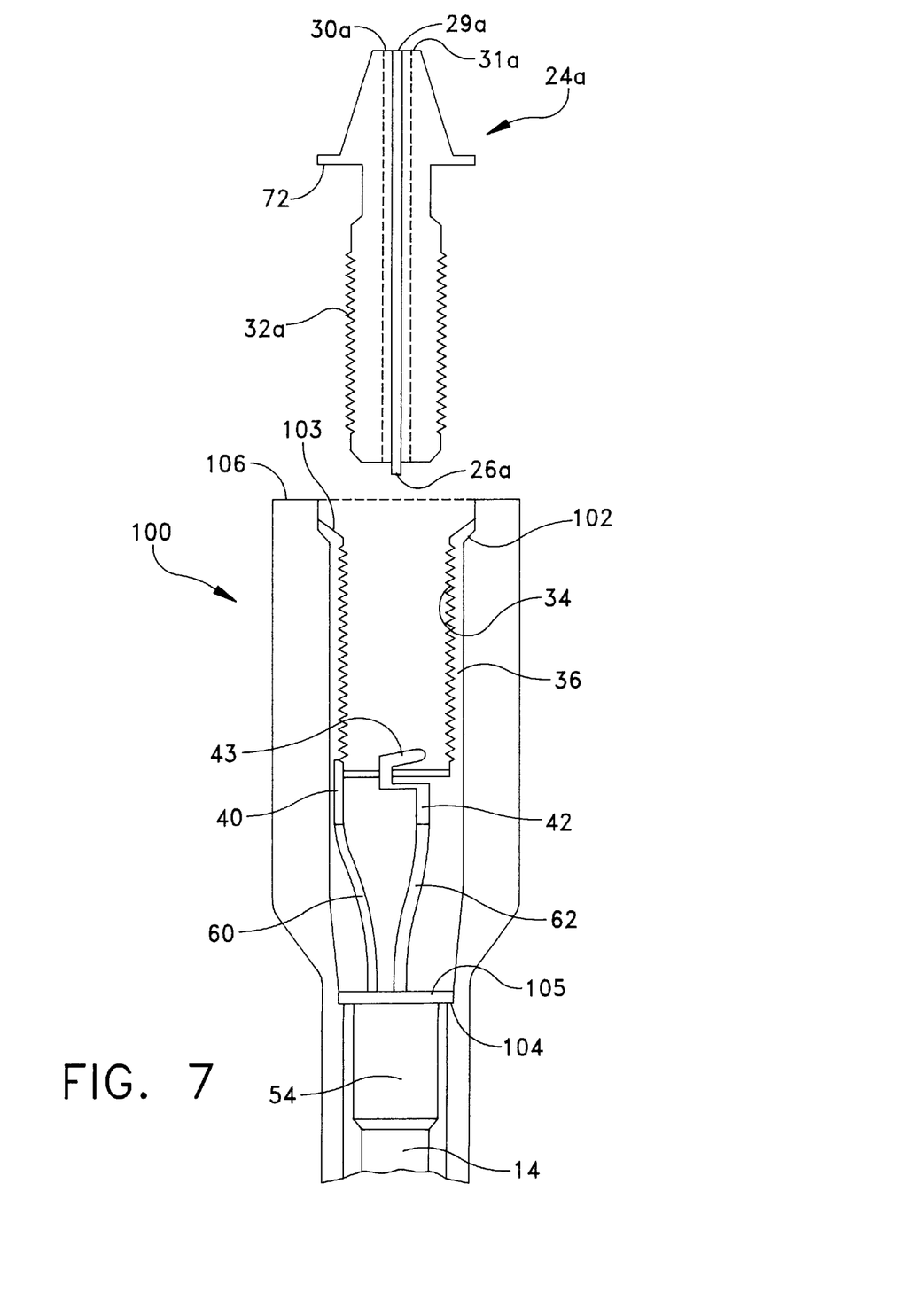
FIG. 7 is a cross-sectional view of an alternative, integral probe having a disposable sensor according to this invention.

Sensor 24a may also be used in conjunction with integrally formed probe handle 100, FIG. 7, in which socket 36 is disposed within probe handle 100 and seated on socket seat 102. Top edge 103 is serrated and pressed into probe handle 100 thereby securing socket 36 to thereto. Cable 14 terminates in bushing 54 which is typically shrink wrapped to cable 14, as noted above. Rim 105 of bushing 54 is seated upon circumferential rim 104 in the interior of probe handle 100. Conductors 60 and 62 are shown to be interconnected with contacts 40 and 42, respectively, as indicated above. When installed sensor 24a threadably engages threads 34 of socket 36 and the underside of rim 72 of sensor 24a seats flush upon the top edge 106 of probe handle 100.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A probe for use with a biophysical skin measurement device having a cable, said probe comprising:

a disposable sensor device;

a handle for receiving the measurement device cable;

a socket on said handle electrically interconnected with the measurement device cable; and means for removably engaging said disposable sensor device and said socket; when engaged, said sensor device being electrically interconnected with the cable through said socket for providing measurement signals to the biophysical skin measurement device.

2. The probe of claim 1 in which said handle includes means for removably interconnecting a cap with said handle for covering said socket and securing said socket to said handle.

3. The probe of claim 1 in which said means for engaging includes first thread means on said socket and second, complementary thread means on said sensor device for engaging said sensor device and said socket.

4. The probe of claim 1 in which said sensor device and said socket are engaged by means of a friction fit.

5. The probe of claim 1 in which said means for engaging includes two projections on said sensor and two complementary slots in said socket for receiving said projections and securing said projections and sensor to said socket.

6. The probe of claim 1 in which said sensor device is at least partially formed of brass.

7. The probe of claim 1 wherein the measurement device cable has first and second conductors and wherein said sensor device includes a first sensor member for interconnecting with one of the first and second conductors and a second sensor member for interconnecting with the other of the first and second conductors.

8. The probe of claim 7 in which said first and second sensor members are electrical conductors.

9. The probe of claim 7 in which said second sensor member is peripherally disposed about said first sensor member and said first and second sensor members are separated by an insulating member.

10. A probe for a biophysical skin measurement device comprising:

a disposable sensor device;

a handle for receiving a cable from the measurement device;

a threaded socket on said handle electrically interconnected with the cable;

said disposable sensor device having threads complementary to the threads on said socket for removably engaging said threaded socket; when engaged, said sensor device being electrically interconnected with said cable through said socket for providing measurement signals to the biophysical skin measurement device; and a cap for engaging the second end of said handle for covering and securing said socket to said handle.

11. A probe for use with a biophysical skin measurement device with a cable, comprising:

a disposable sensor device including a central conductor, an insulating medium coaxially disposed about said central conductor, and an outer conductor member coaxially disposed about said insulating medium;

a handle for receiving the measurement device cable;

a socket on said handle for removably receiving said sensor device, said socket including a conducting inner wall which is in electrical contact with the outer conductor of the sensor device and a central conductor contact within said socket in electrical contact with said central conductor of the sensor device, the conducting inner wall and the central conductor contact separated by an insulating medium, said conducting inner wall and said central conductor contact being electrically interconnected with the measurement device cable through said socket for providing measurement signals from the sensor to the measurement device.

12. A probe for use with a biophysical skin measurement device with a cable, comprising:

a disposable sensor including a contact surface for contacting a patient's skin, the contact surface including a pair of first and second spaced apart conductors thereon, the sensor further including a single male member extending from said contact surface;

a handle for receiving the measurement device cable;

a socket in said handle including means for removably receiving the male member of the sensor to facilitate the disposability and interchangeability of sensors received therein.

13. The probe of claim 12 in which the first conductor is disposed centrally through the male member, and the second conductor is coaxially disposed about the first conductor and separated therefrom by an insulating medium.

14. The probe of claim 12 in which the male member includes a set of threads thereon and the means for removably receiving includes a complementary set of threads in the socket.

15. The probe of claim 12 in which the male member has a first diameter and the means for removably receiving includes an inner surface of the socket of a second diameter less than the first diameter to receive said male member via a friction fit.

16. The probe of claim 12 in which the male member includes a bayonet projection thereon and the means for removably receiving includes a complementary curved slot in the socket for receiving said bayonet projection.

17. A probe for use with a biophysical skin measurement device comprising:

A) a handle having means for communicating with instrumentation and having at one end a socket having first and second spaced, coaxial electrical contacts formed therein, B) a disposable sensor device having at one end spaced electrodes for contacting the skin and at the other end spaced electrodes for engaging the first and second electrodes in said socket, and C) first and second complementary releasable engagement means attached in said socket at the other end of said sensor for having relative motion between locked and unlocked positions whereby said sensor electrodes contact said socket electrodes when said sensor is positioned in said socket and said releasable means is in the locked position and said sensor is removable from said socket when said releasable means is in the unlocked position.

18. A probe as recited in claim 17 wherein the sensor further includes a single male member extending from said contact surface and said socket in said handle includes means for removably receiving the male member of the sensor to facilitate the disposability and interchangeability of sensors received therein.

19. A probe as recited in claim 18 wherein said first conductor is disposed centrally through said male member, and said second conductor is coaxially disposed about the first conductor and separated therefrom by an insulating medium.

20. A probe as recited in claim 18 wherein said male member includes a set of threads thereon and said means for removably receiving includes a complementary set of threads in said socket.

21. A probe as recited in claim 18 wherein said male member has a first diameter and said removably receiving means includes an inner surface of the socket of a second diameter less than the first diameter to receive said male member via a friction fit.

22. A probe as recited in claim 18 wherein said male member includes a bayonet projection thereon and said removably receiving means includes a complementary curved slot in said socket for receiving said bayonet projection.

* * * * *